(12) United States Patent
Yanase et al.

(10) Patent No.: US 7,323,322 B2
(45) Date of Patent: Jan. 29, 2008

(54) **ETHANOL PRODUCTION FROM TRANSFORMED *ZYMOBACTER* MICROORGANISMS**

(75) Inventors: Hideshi Yanase, Tottori (JP); Kenji Okamoto, Tottori (JP); Takahide Takadera, Ninomiya-machi (JP); Atsuko Sugiura, Yokohama (JP)

(73) Assignee: Kansai Paint Co., Ltd., Hyogo-Ken (JP)

( * ) Notice: Subject to any disclaimer, the term of this patent is extended or adjusted under 35 U.S.C. 154(b) by 406 days.

(21) Appl. No.: 10/901,119

(22) Filed: Jul. 29, 2004

(65) Prior Publication Data
US 2005/0074858 A1  Apr. 7, 2005

(30) Foreign Application Priority Data
Jul. 31, 2003  (JP)  ............... 2003-284154

(51) Int. Cl.
*C12P 7/06* (2006.01)
*C12N 9/26* (2006.01)
*C12N 1/20* (2006.01)
*C12N 15/00* (2006.01)
*C07H 21/04* (2006.01)

(52) U.S. Cl. ............ 435/161; 435/69.1; 435/183; 435/200; 435/201; 435/252.3; 435/320.1; 536/23.2

(58) Field of Classification Search ........... 435/69.1, 435/183, 200, 201, 320.1, 252.3; 536/23.2
See application file for complete search history.

(56) References Cited

U.S. PATENT DOCUMENTS
5,712,133 A  1/1998  Picataggio et al.

FOREIGN PATENT DOCUMENTS
WO  98/45451  10/1998

OTHER PUBLICATIONS

Haan et al. Metab Eng. Jan. 2007;9(1):87-94. Epub Sep. 16, 2006.*
M. Takano et al., "Structure of a β-Glucosidase Gene from *Ruminococcus albus* and Properties of the Translated Product", Journal of Fermentation and Bioengineering, vol. 73, No. 2, pp. 79-88, 1992.

* cited by examiner

*Primary Examiner*—Tekchand Saidha
*Assistant Examiner*—Christian L. Fronda
(74) *Attorney, Agent, or Firm*—Wenderoth, Lind & Ponack, L.L.P.

(57) ABSTRACT

This invention provides transformed microorganisms which can produce ethanol from cellooligosaccharide, by introducing β-glucosidase gene by recombinant DNA method, into microorganisms belonging to genus *Zymobacter* which cannot utilize cellooligosaccharide.

2 Claims, 2 Drawing Sheets

BROAD HOST RANGE VECTOR PLASMID

CONSTRUCTION OF pMFY31-βg

CELLOBIOSE FERMENTATION BY RECOMBINANT Zymobacter palmae Strain

Cellobiose Concentration

BATCH FERMENTATION OF CELLOBIOSE BY RECOMBINANT Zymobacter palmae

SEQUENCE LISTING

<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 1
gcggtcgaca tcaaggtgtg atgttgatta tacc                               34

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 2
cgcgtcgact catgtttgac agcttatcat cgat                               34

ETHANOL PRODUCTION FROM TRANSFORMED *ZYMOBACTER* MICROORGANISMS

TECHNICAL FIELD

This invention relates to a recombinant DNA containing β-glucosidase exogenous gene and to transformed microorganisms containing said recombinant DNA. Said transformed microorganisms can be utilized for effective production of ethanol from cellobiose-containing feedstocks.

BACKGROUND ART

Representative microorganisms used for ethanol production are yeast belonging to genus *Saccharomyces* or bacteria belonging to genus *Zymomonas* or *Zymobacter*. These microorganisms normally produce ethanol efficiently from monosaccharide such as glucose, but are incapable of producing ethanol from oligosaccharide or polysaccharide. In carrying out ethanol production from cellulosic biomass as the feedstock, therefore, it is necessary to first degrade cellulose to monosaccharide which can be fermented by microorganisms. Degradation and saccharification of cellulosic biomass are normally carried out by enzyme process using cellulase or acid saccharification process using sulfuric acid or the like. Whereas, problems are present with these methods such that complete degradation of cellulose to monosaccharide is occasionally found difficult, or excessive reaction to raise the degradation ratio may reduce the sugar recovery and in consequence aggravate ethanol production efficiency.

Accordingly, therefore, for improving yield in ethanol production from biomass feedstocks, it is necessary to introduce β-glucosidase gene into the microorganisms used for ethanol production to construct transformed microorganisms which are capable of producing ethanol on substrate of cellooligosaccharide, a partial decomposition product of cellulose.

Genus *Zymomonas* and genus *Zymobacter* are known to show higher fermentation speed than yeast of genus *Saccharomyces*, and various attempts were made relating to construction of transformed microorganisms using *Zymomonas* bacteria as host cells. For example, U.S. Pat. No. 5,712,133 disclosed transformation of *Zymomonas* bacteria to impart thereto pentose fermenting ability. However, when β-glucosidase gene is introduced into *Zymomonas* bacteria by the method described in said U.S. patent, β-glucosidase is not secreted exocellularly, and furthermore because cellooligosaccharide cannot permeate through cell walls of *Zymomonas*, fermentation of cellooligosaccharide to ethanol is impossible. WO98/45451 disclosed transformation of cellobiose-incorporating gene of bacteria belonging to genus *Klebsiella* into *Zymomonas* to enable intracellular ethanol production from cellobiose, but its ethanol production efficiency is low.

DISCLOSURE OF THE INVENTION

A main object of the present invention is to provide transformed microorganisms capable of producing ethanol from cellooligosaccharide, by introducing β-glucosidase into microorganisms belonging to genus *Zymobacter* which are incapable of utilizing cellooligosaccharide, by recombinant DNA method.

We noticed microorganisms which could produce β-glucosidase and carried out various screening procedures, to successfully obtain enzymes exhibiting broad range of cellooligosaccharide digesting characteristics. Because no host-vector system with *Zymobacter* bacteria was established then, we made concentrative studies on construction of vectors, transformation method and cloning enzyme genes which participate in cellooligosaccharide metabolism, to now discover that use of *Zymobacter* bacteria as the host cells enabled extracellular secretion of transformed β-glucosidase, whereby it becoming possible to exclude the influence of rate controlling by incorporation of substrate and to produce ethanol effectively from fermentation feedstocks containing cellooligosaccharide. The present invention is whereupon completed.

Accordingly, therefore, the present invention provides a transformed *Zymobacter* microorganism into which exogenus gene of β-glucosidase is introduced and which has cellooligosaccharide-fermentative ability, i.e., an ability to produce ethanol on cellooligosaccharide substrate.

The invention also provides recombinant DNA which is constructed by ligating a DNA fragment with a vector, said DNA fragment encoding β-glucosidase derived from β-glucosidase-producing bacterial strain.

Figure 1:
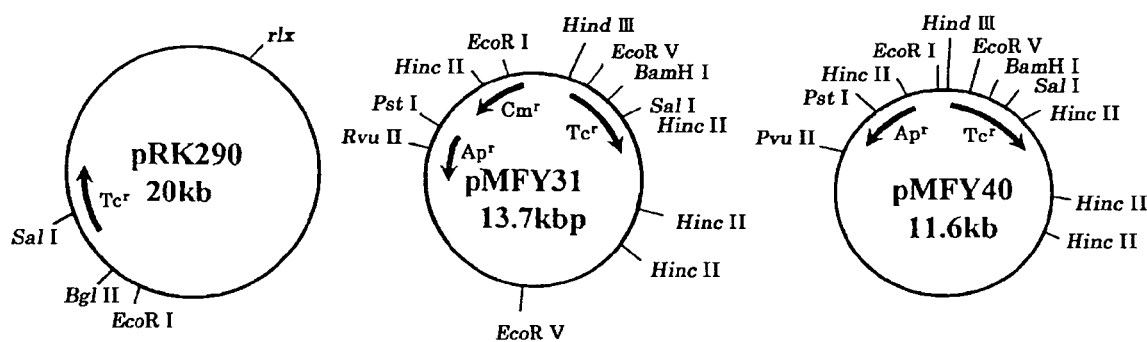
FIG. 1 shows a restriction enzyme cleavage map of a vector plasmid.

Hereinafter the present invention is explained in further details.

In the present invention, a microorganism having β-glucosidase producing ability is used as DNA donor, from which the DNA encoding β-glucosidase is isolated and purified and thereafter cleaved by various methods to provide a DNA fragment containing β-glucosidase gene. Ligating this β-glucosidase gene-containing DNA fragment with a vector-DNA fragment by, for example, DNA ligase, to form a recombinant DNA containing β-glucosidase gene.

The microorganisms used as donors of β-glucosidase gene-containing DNAs are subject to no special limitation, and any of those which can digest cellulose, partially decomposed cellulose or cellooligasoccharide can be used. Whereas, microorganisms belonging to genus *Ruminococcus*, inter alia, *Ruminococcus albus*, are used with particular preference. Other *Ruminococcus* microorganisms or those belonging to genera other than *Ruminococcus* and having β-glucosidase-producing ability, or those which do not have β-glucosidase-producing ability due to abnormality at promoter site or ribosome linkage site but encode on their DNA structural genes of β-glucosidase, can also be used as β-glucosidase gene-containing DNA donors. Furthermore, transformed microorganisms into which β-glucosidase structural genes have been introduced by such means as recombination of genes also are useful as β-glucosidase gene-containing DNA donors.

β-glucosidase gene-containing recombinant DNA can, as introduced into host microorganisms belonging to genus *Zymobacter*, construct transformed microorganisms having β-glucosidase producing ability. So introduced recombinant DNA may be incorporated in the genome of the *Zymobacter* host cells in whole or in part, or the whole or a part may be present on the vector used for the transformation.

Separation and purification of the intended DNA from above donor microorganisms can be effected by any means known per se, for example, the method by Saito, Miura et al. (*Biochem. Biophys. Acta.*, Vol. 72, 619-629, 1963) or modifications thereof, or those using commercialy available DNA extraction kits. Hereinafter a method following the one by Saito, Miura et al. is more specifically explained.

First, the donor microorganism is inoculated into a suitable liquid medium such as an yeast-starch medium containing 0.5% glycine (composition: yeast extract, 0.2%; soluble starch, 1.0%; pH 7.3), followed by culture under agitation at 4-60° C., preferably 30° C., for 8-48 hours, preferably for an overnight. After termination of the culture, the culture solution is subjected to a solid-liquid separation means, for example, centrifugation at 0-50° C., preferably 4° C., and at a rotation rate of 3,000-15,000 rpm, preferably 10,000 rpm.

Thus collected microorganisms are then suspended in a VS buffer (0.15M NaCl, 0.1M EDTA, pH 8.0). After addition of lysozyme, the suspension is allowed to stand at 4-45° C., preferably 37° C., for 0.5-4 hours, preferably an hour, to provide a protoplast liquid. To said liquid TSS buffer (0.1M TRIS, 0.1M NaCl, 1% SDS, pH 9.0) and 5M NaCl are added to dissolve the protoplast, followed by addition of a TE solution (10 mM TRIS, 1 mM EDTA, pH 8.0)-saturated phenol, to effect mild and sufficient suspension. The resultant suspension is centrifuged at 0-50° C., preferably 4° C., and at a rotation rate of 3,000-15,000 rpm, preferably 12,000 rpm, and the formed upper layer (aqueous phase) is suspended in chloroform. The suspension is centrifuged at 0-50° C., preferably 4° C. and at a rotation rate of 3,000-15,000 rpm, preferably 12,000 rpm. Thus formed upper layer (aqueous phase) is again suspended using phenol and chloroform.

Subsequently cold ethanol is added to the suspension, and whereupon formed opaque crude chromosome DNA is recovered. Said DNA is dissolved in SSC buffer (0.15M NaCl, 0.015M sodium citrate) and the solution is dialyzed against SSC buffer for an overnight. To the dialysate ribonuclease is added to a final concentration of 1-50 μg/ml, preferably 10 μg/ml, followed by standing at 4-45° C., preferably 37° C., for 0.5-16 hours, preferably 2 hours. Protease is further added to a final concentration of 0.1-10 μg/ml, preferably 1 μg/ml, followed by standing at 4-45° C., preferably at 37° C., for 15 minutes—8 hours, preferably 30 minutes. Similarly to the above, the system after the standing is treated with phenol and chloroform and dialyzed against SSC buffer to provide a purified chromosome DNA liquid of the donor microorganism.

Thus obtained donor microorganism's DNA is cleaved by, for example, restriction enzyme, and from which DNA fragments of sizes less than 1 kbp are removed by sucrose density gradient method. The remnant can be used as the donor DNA fragment. The restriction enzyme useful in that occasion is subject to no special limitation, but any of various enzymes such as EcoRI which cleaves DNA can be used. Besides the above enzymatic method, DNA can be cleaved by ultrasonic treatment or physical shearing force. A treatment of the donor DNA fragment ends with, for example, Klenow fragment or an enzyme such as DNA polymerase or mung bean nuclease in that occasion is preferred for improving subsequent binding efficiency with vector DNA. Moreover, PCR-amplified products using donor microorganism's DNA or a fragment thereof as a template can also be used as the donor DNA fragments either as they are or after treating them as described above.

On the other hand, while vector DNA fragments are subject to no particular limitation, for example, pRK290, pMFY 40 or pMFY 31 derived from inter-Gram-negative bacterial broad host range plasmid, which are cleaved with restriction enzymes are conveniently used. Vectors other than above-named, for example, broad host range plasmids of known Gram-negative bacteria, may be suitably selected and used. Useful restriction enzymes are not limited to those which produce adhesive ends but various other enzymes which cleave DNAs can be used. Furthermore, vector DNAs can also be cleaved by similar methods to those used for cleaving DNAs of said donor microorganisms.

Thus obtained vector DNA fragments may be treated with alkaline phosphatase in advance of their ligating reaction with aforesaid donor DNA fragments, to improve ligation efficiency with said donor DNA fragments. Furthermore, when a donor DNA fragment is prepared by PCR amplification, its ligating efficiency can be improved by applying in advance a restriction enzyme site-imparting primer such as sal I to both ends of the amplified fragment, and by using a vector fragment which is cleaved with the same restriction enzyme which is used for cleaving the DNA fragment. The ligating reaction between the donor DNA fragment and vector DNA fragment can be conducted by conventionally practiced methods, for example, one using known DNA ligase. For instance, a recombinant DNA can be constructed in vitro by the action of a suitable DNA ligase, after annealing the involved donor DNA fragment and vector DNA fragment. Where necessary, furthermore, the annealed fragments may be introduced into a host microorganism and converted to a recombinant DNA, utilizing in vivo DNA-repairing ability.

As the host microorganism into which the recombinant DNA containing a donor DNA fragment and a vector DNA fragment is to be inserted, any that has ethanol fermentation ability and that can stably retain said recombinant DNA can be used. Whereas, microorganisms belonging to genus *Zymobacter*, generally *Zymobacter palmae*, are conveniently used in the present invention. Method for introducing such a recombinant DNA into the host microorganism is not particularly limited, but when *Zymobacter palmae* or the like is used as the host cell, introduction of the recombinant DNA utilizing electrical stimulation such as electroporation is preferred. Also as to ethanol-producing microorganisms other than *Zymobacter palmae*, for example, *Zymomonas mobilis*, yeast and other hosts, recombinant DNAs can be introduced thereinto by similar methods.

As a growth medium for so obtained transformed microorganisms, for example, where the host microorganism belongs to *Zymobacter*, RM media are frequently used. Where host microorganisms other than *Zymobacter*, such as *Bacillus subtilis*, yeast or the like are used, cultivation in various media suitable for individual host microorganisms can be conducted, and cultivation conditions such as culture temperature can also be suitably designed according to the properties of the used host microorganism. When the vector DNA fragment codes various antibiotic-resistant genes, addition of an adequate amount of a corresponding antibiotic to the medium enables more stable retention of the recombinant DNA which has been introduced. Furthermore, when the used vector DNA is one which codes a gene supplementing auxotrophicity of the host microorganism, stability of the recombinant DNA can similarly be improved by using a medium which contains none of the required nutrient.

The present invention provides a recombinant DNA which enables imparting to *Zymobacter* microorganisms cellobiose fermentation ability by recombinant DNA method; and transformed microorganisms containing the recombinant DNA fragment(s). Use of said transformed microorganisms enables efficient ethanol production from cellobiose-containing sugar solution as the feedstock.

Ethanol production from a cellobiose-containing sugar solution as the feedstock can be conducted through the steps of fermenting a saccharified feedstock containing cellobiose by the action of said cellooligosaccharide-fermentative transformed microorganism, and recovering ethanol from the resultant fermentation liquid, according to, for example, alcoholic fermentation method known per se, using a carrier on which said transformed microorganisms are immobilized.

Immobilization of the transformed microorganisms on said carrier can be effected by any of conventional techniques known per se, for example, entrapping, physical adsorption or covalent bonding.

As the carrier, those preferred have hollow, rugged or porous forms having a large surface area per unit volume, or can swell upon absorbing water, are fluidable and have particle sizes and specific gravity values which do not allow the carrier's easy flowing out of the reaction system. The carrier's configuration may be versatile, for example, special forms of plates, fibers or cylinders, sponge-like structures, particles, blocks or cubes. Of those, fine particles which allow easy ensuring of fluidability and sufficient surface area are preferred. As materials for the carrier, various organic and inorganic materials heretofore used as carrier materials for microorganisms or enzymes can be used, examples of which include inorganic materials such as granular activated carbon, crushed activated carbon, charcoal, zeolite, mica and sand; resin materials such as photo-hardenable resin, polyurethane, polyvinyl alcohol, polyethylene, polyacrylamide, polyester, polypropylene, agar, alginic acid, carrageenan, cellulose, dextran, agarose, ion-exchange resin and the like; porous ceramics such as silica gel; anthracite; and activated carbon or the like mixed in resinous material. These may be used either alone or in combination of two or more.

Said immobilization carriers are normally used as being filled in bioreactors. As bioreactors used for fermentation, there are continuously stirred tank type, packed bed type, membrane type, fluidized bed type and horizontal type, as classified by their operation system. Use of such bioreactors allows continuous fermentation and dispenses with supplying and recovery of the microorganisms, etc. and, therefore, is preferred.

In the occasion of said alcoholic fermentation, various nutrition sources for the microorganisms may be blended in the sugar solutions where necessary. For example, as nitrogen source, yeast extract, corn steep liquor, pepton, meat extract, bonito extract and the like can be used.

Hereinafter the invention is still more specifically explained referring to working examples, it being understood that the invention is not limited thereto.

EXAMPLES

Example 1

Method for Introducing *Zymobacter palmae* Gene

Presence of self-transmissible, multi-drug resistant plasmide DNA in Gram-negative bacteria such as *Escherichia coli* and *Pseudomonas* in general has been reported, and these plasmids are known to propagate among *E. coli* or *Pseudomonas* bacteria. These broad host range multi-drug resistant plasmids and plasmids in which the genic domain participating in the transmissibility and self-replication of these broad host range multi-drug resistant plasmids remains, are occasionally utilized as broad host range vector plasmids (*BIO/TECHNOLOGY*, November, 784-791, 1983). Whereas, vector plasmid of *Zymobacter palmae* and a method for introducing its gene have not yet been developed. We, therefore, selected from broad host range plasmids among Gram-negative bacteria the following three kinds of plasmids of pRK290 and pMFY40 which have Tc-resistance marker and pMFY31 having Cm-resistance marker (*Agric. Biol. Chem.* Vol. 49(9), 2719-2724, 1985) (FIG. 1) as the vector plasmids for introducing genes into *Zymobacter palmae*. Because no gene-introducing method into *Zymobacter palmae* was known, we used electroporation method among generally used methods for gene introduction.

*Zymobacter palmae* (ATCC 51623) was statically cultured for an overnight in RM medium (2.0% glucose, 1.0% Bacto-yeast extract, 0.2% $KH_2PO_4$, pH 6.0). Five (5) ml of the pre-cultured liquid was subcultured in 50 ml of T medium (2.0% glucose, 1.0% Bacto-yeast extract, 1.0% $KH_2PO_4$, 0.2% $(NH_4)_2SO_4$, 0.05% $MgSO_4.7H_2O$, pH 6.0) at 30° C. for 90 minutes. The cultured liquid was centrifuged at 4° C., 300 rpm and for 10 minutes to isolate the microorganism cells to which 20 ml of cooled 10% glycerol was added, followed by suspension and washing. Conducting another centrifugation at 4° C., 3000 rpm for 10 minutes, competent cells were obtained. Two-hundred (200) μl of the competent cells and 10 μl of vector-plasmid DNA solution were mixed on ice, transferred into a cuvette attached to an electroporation device, and electric pulse was applied thereto under such conditions as: voltage 200V, capacitance 250μFD and resistance 200Ω. Immediately then 1 ml of T medium was added to the cuvette, the cells were statically cultured at 30° C. for an hour, and caused to form a colony on a selective medium to which antibiotic to cope with expression of the drug resistant gene in the used broad host range plasmid vector had been added. The transformation efficiency of *Zymobacter palmae* with said plasmid pMFY 40 by the gene introducing method we have developed was about $1 \times 10^6$/μg DNA (Table 1).

TABLE 1

Transformation Efficiency of *Zb. palmae*

| Plasmid used | Transformation efficiency (number of bacteria/μg) |
|---|---|
| pRK290 | $7.45 \times 10^3$ |
| pMFY40 | $1.01 \times 10^6$ |
| pMFY31 | $9.21 \times 10^5$ |

Example 2

Preparation of Recombinant Plasmid Containing β-glucosidase Gene

*Ruminococcus albus*-derived β-glucosidase gene was amplified by PCR using the genome DNA prepared from cells of said bacterium as the template, and the amplified DNA fragment was inserted in the vector plasmid to form a recombinant plasmid. As the primers used in the PCR for amplifying β-glucosidase gene, the following two primers were used, which were so designed, based on known base sequence of said gene (*Nucleic Acids Res.* Vol. 18, 671, 1990), to include the promoter domain conformed in the region upstream of β-glucosidase gene and to be imparted at its two ends SalI site as restriction enzyme cleavage sites:

```
BGN primer:                           (SEQ ID NO: 1)
5'-GCGGTCGACATCAAGGTGTGATGTTGATTATACC-3'

BGC primer:                           (SEQ ID NO: 2)
5-CGCGTCGACTCATGTTTGACAGCTTATCATCGAT-3'.
```

Figure 2:
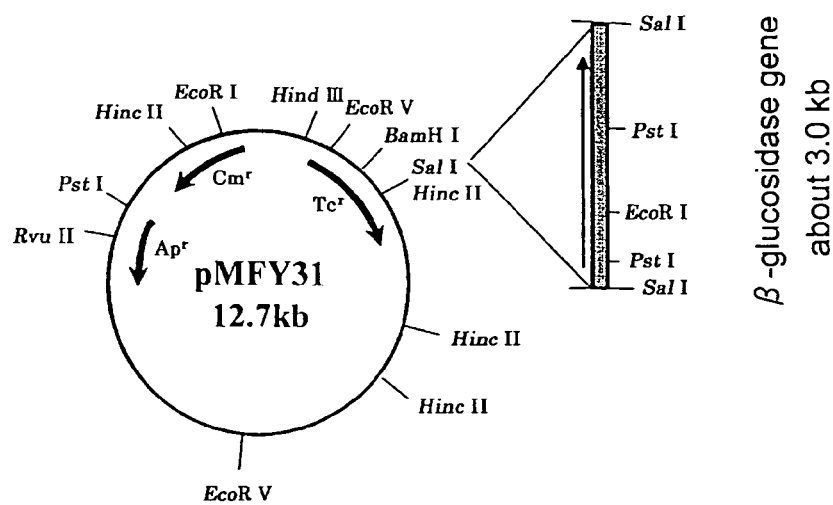
FIG. 2 shows a restriction enzyme cleavage map of a recombinant plasmid containing β-glucosidase gene.

The DNA fragment of about 3.2 kbp containing the promoter and β-glucosidase gene as formed by the PCR was cleaved with restriction enzyme SalI. The DNA fragment after the SalI cleavage was given an alkali phosphatase-treatment and mixed with vector plasmid pMFY31, and they were ligated, utilizing ligase. Ten (10) μl of this ligase reaction solution containing this recombinant plasmid was mixed with 200 μl of *Zymobacter palmae* competent cells as formed in Example 1, and transformed by electroporation method. The transformed strain was selected as blue colony on T plate medium to which 100 μg/ml of ampicillin and 20 μg/ml of 5-bromo-4-chloro-3-indolyl-β-D-glucopyranoside (x-glc) were added as the chemicals. Thus obtained transformed strain has been deposited with National Institute of Advanced Industrial Science and Technology, International Patent Organism Depositary at AIST Tsukuba Central 6, 1-1, Higashi 1-chome, Tsukuba-shi, Ibaraki-ken 305-8566, Japan under deposition number of FERM P-19450 (which has been transferred to international deposition under Budapest Treaty since Jun. 30, 2004 and given a deposition number of FERM BP-10047). The recombinant plasmid into which β-glucosidase gene was inserted was named pMF31-βg (FIG. 2).

Example 3

Cellooligssaccharide Fermentation Ability by Recombinant *Zymobacter palmae* Strain Expression and intracellular localized presence of β-glucosidase in the recombinant *Zymobacter palmae* prepared in Example 2 were investigated.

Each of *Zymobacter palmae*/pMFY31-βg strain, *Zymobacter palmae*/pMFY31 strain and *E. coli* JM109/pMFY-31-βg strain was cultured and cell fractionation of recovered bacterium was conducted (*Science*. Vol. 156(781), 1451-1455, 1967). β-glucosidase activity of each of the cell fractions, i.e., supernatant of culture solution corresponding to extracellular fraction, bacterium washing corresponding to the cell cortex fraction, hypertonic solution washing, osmotic shock solution corresponding to periplasmic fraction, cell membrane fraction and cytoplasm fraction, were measured (*J. Bacteriol.*, Vol.161(1), 432-434, 1985).

β-glucosidase activity in *Zymobacter palmae*/pMFY-31-βg strain was of approximately the same level with that of *E. coli* JM109/pMFY31-βg strain. Furthermore, the expressed β-glucosidase was localized, as for *Zymobacter palmae*/pMFY31-βg, as 29.5% in the bacterium washing, 17.1% in the osmotic shock solution, and 29.5% in the cell-free extract, exhibiting higher secretion ability compared with *E. coli* (Table 2). That is, about 50% of the total expressed activity permeated through the cell membrane and was secreted.

Figure 3:
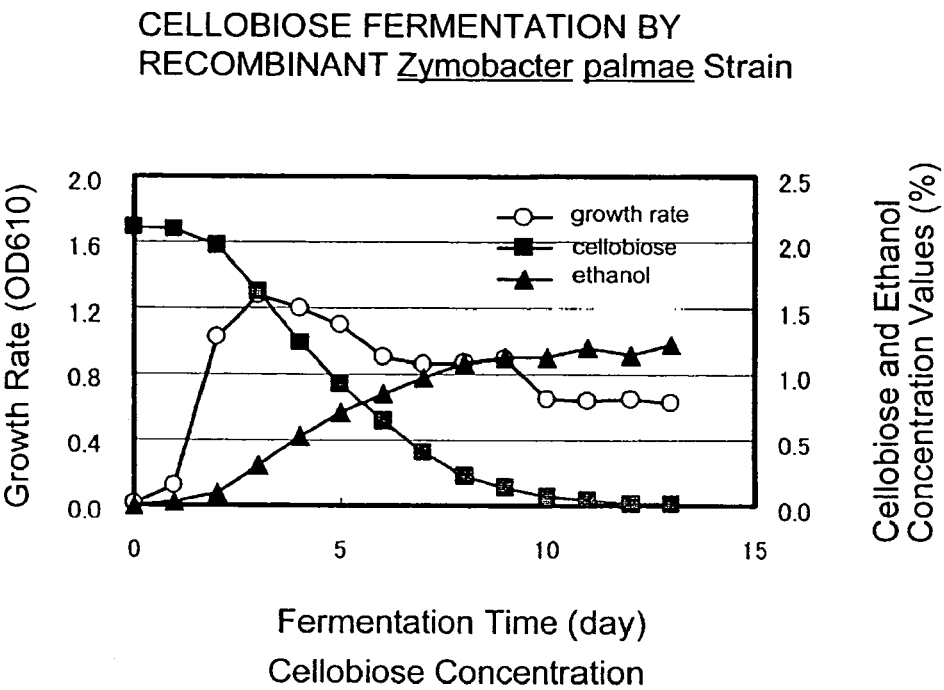
FIG. 3 is a graph showing ethanol productivity by fermentation of cellobiose by recombinant *Zymobacter palmae*.

Recombinant bacterium *Zymobacter palmae*/pMFY31-βg strain was inoculated in culture media each comprising 2% glucose, 2% cellobiose, and 2% glucose+cellobiose as the respective carbon source, and bacterial growth therein and ethanol production with time were measured. In the medium wherein cellobiose was the sole carbon source, the growth rate dropped compared with that in the medium comprising glucose alone, but it consumed 2% cellobiose by the 10th day of the culture to produce ethanol at the theoretical yield (FIG. 3).

TABLE 2

Expression and Intracellular Localization of β-glucosidase in *Zymobacter palmae*

| Cell fraction | *Zb. palmae* T109 (pMFY31) | | *Zb. palmae* T109 (pMFY31-βg) | | *E. coli* JM109 (pMFY31-βg) | |
|---|---|---|---|---|---|---|
| | Activity (U/ml) | Localization (%) | Activity (U/ml) | Localization (%) | Activity (U/ml) | Localization (%) |
| Supernatant of culture solution | <0.01 | — | 0.07 | 6.7 | 0.01 | 1.3 |
| Bacterium washing | <0.01 | — | 0.31 | 29.5 | 0.06 | 7.6 |
| Hypertonic solution washing | <0.01 | — | 0.05 | 4.8 | 0.01 | 1.3 |
| Osmotic shock solution | <0.01 | — | 0.18 | 17.1 | 0.02 | 2.5 |
| Cytoplasmic fraction | <0.01 | — | 0.31 | 29.5 | 0.59 | 74.7 |

TABLE 2-continued

Expression and Intracellular Localization of β-glucosidase in *Zymobacter palmae*

| Cell fraction | Zb. palmae T109 (pMFY31) | | Zb. palmae T109 (pMFY31-βg) | | E. coli JM109 (pMFY31-βg) | |
|---|---|---|---|---|---|---|
| | Activity (U/ml) | Localization (%) | Activity (U/ml) | Localization (%) | Activity (U/ml) | Localization (%) |
| Membrane fraction | <0.01 | — | 0.13 | 12.4 | 0.10 | 12.7 |
| Total activity | | | 1.05 | | 0.79 | |

1 unit: amount of the enzyme to release p-nitrophenol from 1 μmole of p-nitrophenyl-β-D-glucopyranoside per minute Example 4

Figure 4:
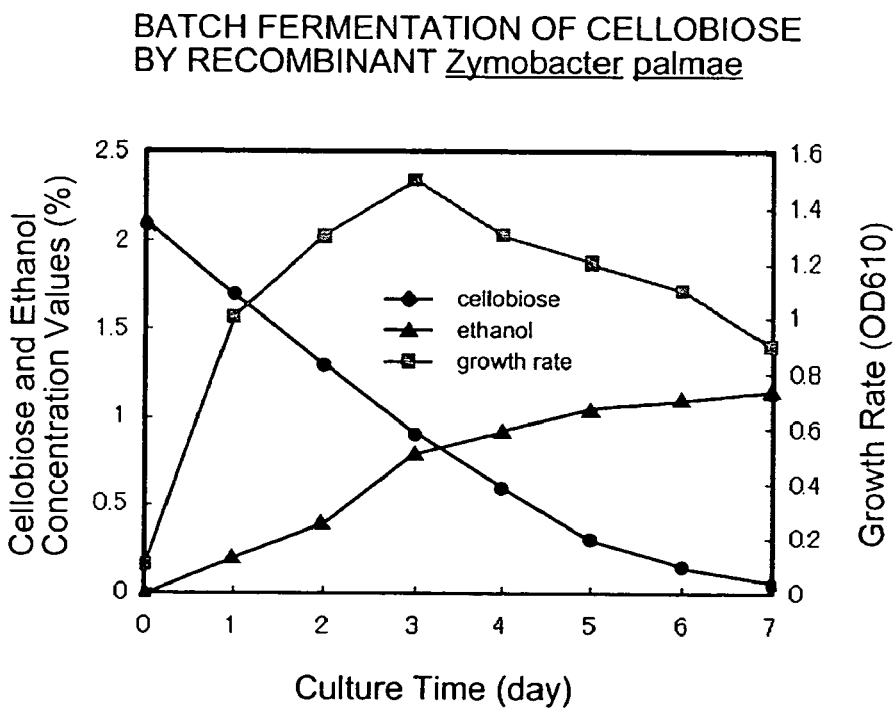
FIG. 4 is a graph showing ethanol productivity by batch fermentation of cellobiose by recombinant *Zymobacter palmae*.

Recombinant *Zymobacter palmae* FERM P-19450 (FERM BP-10047) strain was inoculated in CB medium (2.0% cellobiose, 1.0% yeast extract, 1.0% KH$_2$PO$_4$, 0.2% (NH$_4$)$_2$SO$_4$, 0.05% MgSO$_4$.7H$_2$O, pH 6.0) using biomass partially saccharified liquid-derived cellobiose as the sole carbon source, and statically cultured for five days to provide a pre-culture solution. For the main culture the above CB medium was used, in which 10% to the main culture CB medium of said pre-culture solution was inoculated, followed by culturing under mild agitation at 30° C. Growth rate of the inoculated cells, cellobiose concentration and ethanol concentration changes with time were regularly measured, to confirm that substantially all of the cellobiose was consumed by 7 days' culture and ethanol was produced at the theoretical yield (FIG. 4).

Example 5

Using a medium prepared by adding yeast extract, KH$_2$PO$_4$, (NH$_4$)$_2$SO$_4$ and MgSO$_4$.7H$_2$O to a sugar solution (10% glucose, 1% cellobiose) formed by sulfate saccharification of waste wood, in the amounts, respectively, of 1.0%, 1.0%, 0.2% and 0.05% to the sugar solution and adjusting pH to 6.0, continuous fermentation was conducted. Recombinant *Zymobacter palmae* FERM P-19450 (FERM BP-10047) was immobilized on photo-hardenable resin ENTG™-3800 (manufactured by Kansai Paint) by entrapping. For the continuous fermentation a draft tube-formed bioreactor (fluidized bed type) was used. After throwing the immobilization carrier into the reactor at a fill ratio of 20%, the medium was continuously poured into the reactor from a lower part. A fluidized bed was formed by collecting the carbon dioxide formed by the fermentation and recycling it into the reactor from a lower part thereof. The continuous fermentation could be carried out at 30° C. and at a dilution ratio D equaling 0.1 h$^{-1}$ stably for more than a month, with the sugar consumption ratio not lower than 99% and ethanol yield not less than 95%.

Example 6

Continuous fermentation was conducted using a medium prepared by adding yeast extract, KH$_2$PO$_4$, (NH$_4$)$_2$SO$_4$ and MgSO$_4$.7H$_2$O to a sugar solution (8% glucose, 2% cellobiose) formed by enzymatic saccharification of waste paper-derived cellulose with cellulase, in the amounts, respectively, of 1.0%, 1.0%, 0.2% and 0.05% to the sugar solution and adjusting pH to 6.0. Recombinant *Zymobacter palmae* FERM P-19450 (FERM BP-10047) cells were immobilized on cylindrical (2 mmφ×3 mm) polypropylene carrier which was thrown into the cell suspension. For the continuous fermentation a fixed bed bioreactor (packed bed type) was used. After throwing the immobilization carrier into the reactor at a fill ratio of 80%, said medium was continuously supplied into the reactor from a lower part. The continuous fermentation could be carried out at 30° C. and at a dilution ratio D equaling 0.2 h$^{-1}$ stably for more than a month, with the sugar consumption ratio not lower than 99% and ethanol yield not less than 95%.

The invention claimed is:

1. An isolated *Zymobacter palmae* strain transformed with a polynucleotide encoding β-glucosidase obtained from *Ruminococcus albus* using PCR primers of SEQ ID No. 1 and SEQ ID No. 2, said transformed strain having been deposited at National Institute of Advanced Industrial Science and Technology, International Patent Organism Depositary under deposit accession number FERM BP-10047.

2. A process for producing ethanol, which comprises fermenting a saccharification material containing cellobiose using the transformed *Zymobacter palmae* strain of claim 1, and recovering ethanol from the resultant fermented solution.

* * * * *